United States Patent [19]

Thompson et al.

[11] Patent Number: 5,637,348

[45] Date of Patent: Jun. 10, 1997

[54] METHOD OF INCREASING THE SPF RATING AND COMPOUNDS SUITABLE FOR INCREASING THE SPF RATING OF FIBRE OR FABRIC

[75] Inventors: Bernard L. Thompson, Curl Curl; Michael T. Pailthorpe, Roseville, both of Australia

[73] Assignee: Clariant Finance (BVI) Limited, Virgin Islands (Br.)

[21] Appl. No.: 387,768

[22] PCT Filed: Aug. 12, 1993

[86] PCT No.: PCT/AU93/00412

§ 371 Date: Jun. 15, 1995

§ 102(e) Date: Jun. 15, 1995

[87] PCT Pub. No.: WO94/04515

PCT Pub. Date: Mar. 3, 1994

[30] Foreign Application Priority Data

Aug. 12, 1992 [AU] Australia .................. PL4068
Oct. 9, 1992 [AU] Australia .................. PL5205

[51] Int. Cl.⁶ .................................................. D06B 1/00
[52] U.S. Cl. .................. 427/160; 8/115.51; 8/116.1; 8/181; 8/190; 8/127.5; 8/127.6; 8/636; 8/648; 252/8.61; 252/8.91; 427/394; 427/430.1; 427/439; 428/913; 442/133
[58] Field of Search .................. 252/8.6, 8.8, 8.61, 252/8.91; 8/115.51, 115.6, 116.1, 181, 189, 190, 127.5, 127.6, 648, 636; 428/224, 260, 288, 289, 913; 427/160, 394, 430.1, 439

[56] References Cited

U.S. PATENT DOCUMENTS

| | | | |
|---|---|---|---|
| 2,719,846 | 10/1955 | Burtner | 544/326 |
| 2,720,480 | 10/1955 | Wolf | 514/245 |
| 2,820,032 | 1/1958 | Hill | 544/211 |
| 3,198,797 | 8/1965 | Dexter et al. | 544/211 |
| 3,666,759 | 5/1972 | Crabtree | 544/211 |
| 4,189,576 | 2/1980 | Altorfer et al. | 544/211 |
| 4,361,698 | 11/1982 | Otten et al. | 544/211 |
| 4,740,597 | 4/1988 | Franke et al. | 544/211 |
| 4,855,410 | 8/1989 | Oxenius et al. | 534/591 |
| 4,857,305 | 8/1989 | Bernhardt | 424/59 |
| 4,900,813 | 2/1990 | Tzikas et al. | 534/591 |
| 4,939,243 | 7/1990 | Meininger et al. | 534/625 |
| 5,332,813 | 7/1994 | Hoppe et al. | 544/204 |

FOREIGN PATENT DOCUMENTS

| | | |
|---|---|---|
| 0410055 | 1/1991 | European Pat. Off. . |
| 0445076 | 9/1991 | European Pat. Off. . |
| 445076 | 9/1991 | European Pat. Off. . |
| 3330547 | 3/1985 | Germany . |
| 3740650 | 6/1989 | Germany . |
| 3-158103 | 7/1991 | Japan . |
| 872313 | 7/1961 | United Kingdom . |
| 889292 | 2/1962 | United Kingdom . |
| 1444426 | 7/1976 | United Kingdom . |

OTHER PUBLICATIONS

Derwent Abstract 91-242625 corresponding to JP 3-158103 (Jul. 1991).

The Chemistry and Application of Dyes Waring et al., eds., p. 87, Plenum Press, New York 1990 No Month.

D.J. Brown, The Chemistry of Heterocyclic Compounds, The Pyrimidines, pp. 191, 312, and 543, Interscience Publishers 1962 No Month.

D.J. Brown, The Chemistry of Heterocyclic Compounds, The Pyrimidines, Supplement 1, Table XXXI, (T81), Wiley-Interscience Publishers 1970 No Month.

D.J. Brown, The Chemistry of Heterocyclic Compounds, The Pyrimidines, Supplement II, pp. 570 and 571, John Wiley & Sons No Date.

The Chemistry of Synthetic Dyes, vol. VI Reactive Dyes, K. Venkataraman, ed., pp. 37, 40, 104, & 133, Academic Press New York 1972 No Month.

N. Asano, "An Ultraviolet (UV) and Heat Radiation-Shielding Fiber", Kato Giyutu, vol. 26, No. 10, 642-646, Jan. 1991 + 2-page uncertified translation of portions thereof.

M. Ichikawa, "UV Protective Substrate 'NaviUV'"; Kato Giyutu, pp. 637-641, Oct. 1991 + 2-page uncertified translation of portions thereof.

Primary Examiner—Anthony Green
Attorney, Agent, or Firm—Robert S. Honor; Carl W. Battle; Gabriel Lopez

[57] ABSTRACT

The present invention provides a method of increasing the sun protection factor (SPF) rating of a fiber or fabric, comprising the steps of providing a UVR absorber, applying the UVR absorber to a fabric, whereby the UVR absorber is attached to the fiber and an application of less than 3% UVR absorber on weight of fiber produces an SPF rating of greater than 20 for the UVR absorber and fabric combination.

8 Claims, 1 Drawing Sheet

FIGURE 1

METHOD OF INCREASING THE SPF RATING AND COMPOUNDS SUITABLE FOR INCREASING THE SPF RATING OF FIBRE OR FABRIC

TECHNICAL FIELD

The present invention relates to a method of increasing the sun protection factor (SPF) rating and compounds suitable for increasing the SPF rating of fibre or fabric.

BACKGROUND OF THE INVENTION

Last year over 1,000 Australians died of skin cancer while two thirds of the Australian population will develop some form of skin cancer at some stage in their lives. This year it is anticipated that 150,000 Australians will go to their doctors for the examination and treatment of some form of sun induced skin cancer.

It is interesting to note that, in spite of public education campaigns and the widespread use of "Sun-Block" creams, skin cancer rates have not changed in recent years.

Even though there has been various sun protection aids in the market for many years, the present inventors have found that most consumers do not fully understand what an SPF rating means.

A typical fair skinned person, on a summers day in Australia, at noon (1:00 pm Eastern Summer Time), would "burn" in approximately 15 minutes (i.e. 0.25 hours). If this person applied "sun block" cream (or textile) of SPF 4 (if available), then this person would burn in 4 times 15 minutes, viz 1 hour. It is important to note, however, that this person would have received the same total UVR dose either way.

A common way of avoiding sunburn when performing activities in a sunny environment is to apply a sunburn cream to skin. The problem with such a solution however is that most sunburn creams only provide UVR protection up to an SPF rating of 15+ and therefore prolonged exposure to the sun can still cause damage to a persons skin despite the use of a sunburn cream.

In addition, avoiding exposure of skin to the sun by wearing clothing, for example a T-shirt, does not necessarily provide adequate UVR protection for the wearer, when the wearer is exposed to the sun for prolonged periods. This problem is compounded by the fact that in hot climates it is desirable to have light weight clothing, which typically has a low SPF rating.

For example, for materials having a density of less than 200 grams per square meter, nylon has an SPF rating of between 10 and 15, polyester has an SPF rating of between 13 and 17, wool has an SPF rating of 10–20 and cotton has an SPF rating of between 5 and 15. It follows therefore that a person wearing a shirt made of light weight fabric such as cotton or wool, if exposed to the sun for prolonged periods can still be subjected to significant doses of UVR radiation. Thus, over an extended period of time, a person working in the sun and wearing a cotton T-shirt can still be exposed to a significant cumulative dose of UVR radiation.

Essentially, the SPF protection of a fabric depends on the "Cover Factor" of the fabric. The Cover Factor may be defined as the percentage of the fabric surface that is covered by the yarns of the fabric. If one assumes that the yarns employed to weave or knit the fabric are completely opaque to UVR radiation (which is not the case in reality) then the fabric SPF would be simply related to Cover Factor by the following formula:

$$\text{Fabric SPF} = \frac{100}{100 - \text{Cover Factor}}$$

DISCLOSURE OF THE INVENTION

In one aspect, the present invention provides a method of increasing the SPF rating of a fibre or fabric, comprising the steps of providing a UVR absorber, applying the UVR absorber to a fabric having a density of less than 200 grams per square meter, whereby the UVR absorber is attached to the fibre and an application of less than 3% UVR absorber on weight of fibre produces an SPF rating of greater than 20 for the UVR absorber and fabric combination.

In one embodiment, the present invention provides a method of increasing the SPF rating of a fibre or fabric, comprising the steps of providing a UVR absorber, applying the UVR absorber to a fabric having a density of less than 200 grams per square meter, whereby the UVR absorber is attached to the fibre and an application of less than 2% UVR absorber on weight of fibre produces an SPF rating of greater than 20 for the UVR absorber and fabric combination.

Preferably the UVR absorber enters the fibre and fixes itself to the fibre.

It is preferred that the combination of fabric and UVR absorber is water-fast so that washing of the fabric after its SPF rating has been increased by the addition of the UVR absorber, does not cause any significant drop in the SPF rating of the fibre.

Preferably the UVR absorber comprises a substituted benzotriazole.

The fibre may be wool, nylon, polyester, cotton or any other synthetic fibre or composite thereof.

It is preferred that when the fibre is nylon the UVR absorber is Fadex F (registered trade name of Sandoz).

It is preferred that when the fibre is polyester, the UVR absorber is Fadex F (registered trade name of Sandoz).

Preferably the SPF rating is increased by greater than 30 for non-composite fabrics and by greater than 9 for composite fabrics.

It is preferred that when the fibre is wool the UVR absorber is CIBAFAST W (registered trade name of CIBA-GEIGY).

It is preferred that when the fibre is a secondary cellulose acetate or triacetate, the UVR absorber is Fadex F (registered trade name of Sandoz).

In a second aspect, the present invention provides a method of increasing the SPF rating of cellulosic or protein fibre or fabric, comprising applying to cellulosic or protein fibre or fabric one or more compounds of formula (I)–(IV):

(II)

(III)

(IV)

wherein A is —NH— or —SO$_2$— and when A is —NH—, B is selected from a compound of formula (i)–(vii) as follows:

(i)

(ii)

(iii)

(iv)

(v)

—CO—C=CH$_2$ (vi)
      |
      Br —CO—CH=CH$_2$ (vii)

and where A is —SO$_2$—, B is selected from a compound of formulae (viii)–(x) as follows:

(viii) —CH=CH—OSO$_3$H
(ix) —CH$_2$—CH$_2$—OSO$_3$H
(x) —NH—CH$_2$—CH$_2$—OSO$_3$H wherein R is independently selected from —OH, —NH$_2$, —SO$_3^-$M$^+$, —SO$_3$H, alkyl, alkoxy, alkanoyl, alkylcarboxylate, —S—alkyl, —CF$_3$, —N-di-alkyl;
n=0, 1, 2, 3 or 4

M$^+$=cation
X=H, or Cl, F, Br and is independently selected
Y=X or R.

In a third aspect, the present invention provides a compound of formula (I), (II), (III) or (IV)

(I)

(II)

(III)

(IV)

wherein A, B, R and n are as defined above; but excluding the compound of formula (III) where A is —NH—, B is a compound of formula (ii);
X is Cl, n is 2 and one R is in the 3-position of the phenyl ring and is —CH$_3$ and the other R is in the 4-position and is —SO$_3^-$Na$^+$.

In a fourth aspect, the present invention provides a process of preparing a compound of formula (I)–(IV) which comprises:

1) for preparing compounds of formula (I)–(IV) where A is —NH— and B is a compound of formula (i), (ii), (iii), (iv) or (v): reacting the appropriate amine of formula (I), (II), (III) or (IV) with a chloro derivative of a compound of formula (i), (ii), (iii), (iv) or (v);

2) for preparing compounds of formula (I)–(IV) wherein A is —NH— and B is a compound of formula (vi) or (vii):
   (i) reacting the appropriate amine of formula (I), (II), (III) or (IV) with —CH$_2$BrCHBrCOCl to provide the dibromopropionyl derivative;
   (ii) debromination with potassium hydroxide or the like to provide the bromoacrylamido derivative of formula (vi); and
   (iii) further debromination with potassium hydroxide or the like to provide the acrylamido derivative of formula (vii);

3) for preparing compounds of formula (I)–(IV) where A is —SO$_2$— and B is a compound of formula (viii) or (ix):
   (i) esterification of the appropriate B-hydroxethyl sulphone derivatives of the compounds of formulae (I) to (IV) with sulphuric acid or the like to provide compounds of formula (I) to (IV) where B is a compound of formula (viii) and;
   (ii) dehydration in the presence of a base to form the vinyl compound of formula (ix);

4) for preparing compounds of formula (I)–(IV) where A is —SO$_2$— and B is a compound of formula (x):

esterification of the appropriate B-hydroxyethyl aminosulphone derivative of the compounds of formulae (I)–(IV) with sulphuric acid or the like (as in 3(i) above) to provide compounds of formula (I)–(IV) where B is a compound of formula (x).

Preferred compounds of formula (I)–(IV), designated as P-Q for convenience combination of P with any Q as follows:

P

Q

-continued

6. —NH—CO—C(Br)=CH$_2$

7. —NH—CO—CH=CH$_2$

8. —SO$_2$—CH=CH—OSO$_3$H

9. —SO$_2$—CH$_2$—CH$_2$—OSO$_3$H

10. —SO$_2$—NH—CH$_2$—CH$_2$—OSO$_3$H

The starting materials for the above processes 1 to 4 are known compounds and are readily available. Given the compounds to be reacted, the skilled addressee would be able to readily determine the reaction conditions.

Compounds of formulae (I)–(IV) are useful as UVR absorber compounds and can be applied to fabrics of any weight. Typically, they are suitable for application to light weight summer fabrics and to heavier fabric up to and including industrial weight fabrics.

In a fifth aspect, the present invention provides a method of increasing the SPF rating of cellulosic or protein fibre or fabric, comprising the steps of applying a compound of formula (I)–(IV) to cellulosic or protein fibres or fabric having a density of less than 200 g/m$^2$ whereby an application of less than 3% of a compound of formula (I)–(IV) on weight of fibre or fabric produces an SPF rating of greater than 20.

In another embodiment, the present invention provides a method of increasing the SPF rating of cellulosic or protein fibre or fabric, comprising the steps of applying a compound of formula (I)–(IV) to cellulosic or protein fibres or fabric having a density of less than 200 g/m$^2$ whereby an application of less than 2% of a compound of formula (I)–(IV) on weight of fibre or fabric produces an SPF rating of greater than 20.

Cellulosic fibres may be any fibres of plant origin such as cotton, viscose, flax, linen, rayon or the like or composites thereof. Also, composites can be with polyester, polyamides, polyacrylonitriles or the like.

Protein fibres may be any fibres of animal origin such as wool, mohair, silk, cashmere, angora or the like or composites thereof. Also, composites can be with polyester, polyamide or the like.

It is preferred that when the fibre is protein, a compound of formula (I)–(IV) where B is (ii), (iv), (v), (vi), (vii), (viii) or (ix) is applied.

It is preferred that when the fibre is cellulosic, a compound of formula (I)–(IV) where B is (i), (ii), (iii) or (iv) is applied.

Preferably, the cellulosic fibre is cotton and the protein fibre is wool.

Typically, a 2% on weight of fibre application of compound of formula (III) will increase the SPF rating of a 120 g/m$^2$ 100% cotton fabric from 15+ to 30+.

Typically, a compound of formula (I)–(IV) enters the fibre and fixes itself to the fibre with the reactive group B of compounds of formula (I)–(IV) reacting with the fibre.

Typically, for composite fabrics, sequential application of UVR absorber relevant for each component of the composite increases the SPF rating of the composite fabric by greater than 30.

For example, for cotton/polyester fabric, sequential application of UVR absorber for cotton followed by the application of UVR absorber for polyester or vice versa, increases the SPF rating of the fabric by greater than 30.

In a sixth aspect, the present invention provides an article of clothing comprising a plurality of fibres and a UVR absorber, wherein the plurality of fibres have a density of less than 200 grams per square meter and the SPF rating of the article has been increased to at least 20 by the addition of less than 3% UVR absorber on weight of fibre.

Preferably, in the article of clothing comprising a plurality of fibres and a UVR absorber, wherein the plurality of fibres have a density of less than 200 grams per square meter, the SPF rating of the article has been increased to at least 20 by the addition of less than 2% UVR absorber on weight of fibre.

According to another aspect of the present invention, there is provided an article of clothing comprising a plurality of fibres and a UVR absorber of compound of formula (I)–(IV).

Preferably, in the article of clothing with the UVR absorber of compounds of formula (I)–(IV), the plurality of fibres has a density of less than 200 g/m².

Preferably, in the article of clothing with the UVR absorber compound of formula (I)–(IV) wherein the plurality of fibres have a density of less than 200 g/m², the SPF rating of the article has been increased to at least 20 by the addition of less than 3% UVR absorber on weight of fibre.

More preferably, in the article of clothing with the UVR absorber compound of formula (I)–(IV) wherein the plurality of fibres have a density of less than 200 g/m², the SPF rating of the article has been increased to at least 20 by the addition of less than 2% UVR absorber on weight of fibre.

Preferably, the fibre comprising the UVR absorber is colour-fast and light-fast.

Typically, the UVR absorber is bonded to the fibre by virtue of the reaction of compounds of formula (I)–(IV) with the fibre.

The present invention also provides a formulation suitable for application to cellulosic or protein fibres or fabrics comprising a compound of formula (I)–(IV) in a suitable carrier.

Preferably, the SPF rating is increased to greater than 30.

It is preferred that the combination of fibre or fabric and UVR absorber is water-fast so that washing of the fabric after its SPF rating has been increased by the addition of the UVR absorber compounds of formula (I)–(IV), does not cause any significant drop in the SPF rating of the fibre or fabric.

The fibre or fabric may also comprise a dye or pigment or other coatings or finishes known in the industry.

It is preferred that the UVR absorber be transparent to visible radiation when applied to the fibre or fabric. Typically, once applied the original colour of the fabric or fibre is substantially unaffected.

The combination of fabric and UVR absorber is preferably light-fast. The fibre or fabric treated with the UVR absorber is preferably colour-fast to washing.

The fibre my be wool, nylon, polyester, cotton or any other synthetic fibre or composite thereof.

Preferably the UVR absorber is bonded to the fibres by virtue of an affinity the UVR absorber has for the fibres.

Preferred embodiments of the present invention will now be described by way of example only with reference to the accompanying experimental results.

BEST MODES FOR CARRYING OUT THE INVENTION

SYNTHESIS METHODS

Example 1

Synthesis via 1,3,5-s-triazine (cyanuric chloride)

The selected amine compound (1 mole as a slurry in 100 ml water [ice cold]) is added slowly to cyanuric chloride (1 mole as a slurry in 200 ml acetone [ice cold]), whilst maintaining the pH of the solution at 7 by the addition of 2N sodium hydroxide. The reaction mixture is stirred for 1.5–2.0 hours (whilst maintaining the temperature below 5° C.) after which time the reaction is judged to be complete once the pH stabilises at 7 and the test for free amine (TLC) is negative. The product is then filtered off, washed thoroughly with acetone and then oven dried.

Example 2

Synthesis via 2,4,6-trifluoro-5-chloro-pyrimidine

The selected amine compound (1 mole as a slurry in 100 ml water [ice cold]) is added slowly to 2,4,6-trifluoro-5-chloro-pyrimidine (1 mole dissolved in 300 ml acetone [ice cold]), whilst maintaining the pH of the solution at 7 by the addition of a saturated aqueous solution of sodium carbonate. The reaction mixture is stirred for 1.5–2.0 hours (whilst maintaining the temperature below 5° C.) after which time the reaction is judged to be complete once the pH stabilises at 7 and the test for free amine (TLC) is negative. The product is then filtered off, washed thoroughly with acetone and then oven dried.

Example 3

Synthesis via epichlorohydrin

The selected amine compound (1 mole as a slurry in 100 ml ethanol [ice cold]) is added slowly to epichlorohydrin (1 mole dissolved in 100 ml ethanol [ice cold]), whilst maintaining the pH of the solution at 7 by the addition of a saturated aqueous solution of sodium carbonate. The reaction mixture is stirred for 1.5–2.0 hours (whilst maintaining the temperature below 5° C.) after which time the reaction is judged to be complete once the pH stabilises at 7 and the test for free amine (TLC) is negative. The product is then filtered off, washed thoroughly with acetone and then oven dried.

Example 4

Synthesis via 2,3-dibromopropionic acid chloride 2,3-dibromopropionic acid chloride (1 mole) is added dropwise to a solution of the selected amine (1 mole as a slurry in 100 ml acetone containing 0.5 mole pyridine) at 30°–45° C. The reaction mixture is then stirred for 14 hours at room temperature. The pyridine and acetone solvents are then removed by vacuum evaporation.

The intermediate 2,3-dibromopropionamide compound:

is then treated as follows:

1 mole of the 2,3-dibromopropionamide compound is charged into 500 ml ethanol and heated to 60° C. Then add dropwise a solution consisting of 1.6 mole of potassium hydroxide in 250 ml ethanol. The temperature of the reaction vessel is then raised from 60° to 68° C. Upon completion of the addition, the reaction mixture is heated under reflux for 4 hours.

Example 5

Synthesis of 2,4-dichloro-s-triazin-6-yl-p-aminophenyl-sulphonic acid sodium salt (dihydrate)

p-aminophenyl-sulphonic acid (sulphanilic acid) (26 g as a slurry in water) was added slowly to cyanuric chloride (28 g as a slurry in 200 ml acetone containing circa 100 g ice), whilst maintaining the pH of the solution at 7 by the addition of 2N sodium hydroxide. The reaction mixture was stirred for 1.5–2.0 hours after which time the reaction was judged to be complete once the pH had stabilised at 7 and the test for free amine (TLC) was negative. The product was filtered off, washed thoroughly with acetone and then oven dried. The yield was 92%.

TLC showed that the product was free of starting materials. The IR spectrum and elemental analysis results confirmed the authenticity of the product. The elemental analysis results are given in the following table.

|  | Carbon | Hydrogen | Nitrogen |
|---|---|---|---|
| Expected | 27.40 | 1.72 | 21.30 |
| Found | 27.53 | 1.84 | 21.25 |

Example 6

Synthesis of 2,4-dichloro-s-triazin-6-yl-amino-8-naphthol-3,6-disulphonic acid sodium salt (dihydrate)

38 g 1-amino-8-naphthol-3,6-disulphonic acid was dissolved in 1N sodium bicarbonate solution, the solution was diluted to 500 ml and neutralised with acetic acid. This solution and 2N sodium bicarbonate solution were dropped simultaneously into a well stirred suspension of cyanuric chloride (20.2 g) in acetone and ice water (100 ml 1:1) at 0° C. over 3 hours. The reaction was judged to be complete when the pH stabilised at 7 and the test for free amine (TLC) was negative. The reaction solution was rotary evaporated (at 40° C.) to reduce solvents. The product was then filtered off and vacuum dried at room temperature. The yield was 70%.

TLC showed that the product was free of starting materials. The IR spectrum and elemental analysis results confirmed the authenticity of the product. The elemental analysis results are given in the following table.

|  | Carbon | Hydrogen | Nitrogen |
|---|---|---|---|
| Expected | 33.42 | 1.72 | 11.99 |
| Found | 32.98 | 1.31 | 11.45 |

Characterisation of Products

The products were characterised using a combination of melting points, Infra-red [IR] spectra, elemental analyses and thin layer chromatography [TLC]. Melting points were determined on a Gallenkamp Melting Point Apparatus. IR spectra were recorded on a Hitachi Model 260-10 Infrared Spectrophotometer and referred to Nujol mulls. Elemental analyses were conducted (under contract) by the School of Chemistry, University of New South Wales. TLC was carried out using Merck 60$F_{254}$ Silica Gel TLC foils. A variety of eluents including acetone, water-saturated butanol and ethanol were used. The chromatograms were visualised at 254 nm with a Universal UV Lamp (CAMAG Muttenz Schweiz).

APPLICATION METHODS

1. Di-chloro-s-triazine UV absorber derivatives on cotton

Example 7

These compounds may be applied to cotton by either exhaustion or pad methods

A suitable exhaustion method is as follows:

Apply 2% owf absorber compound, 10% owf sodium chloride and 0.1% owf wetting agent (e.g. a nonylphenyl polyethoxylate); LR 30:1; for 30 minutes at 30° C. Then add 5% owf sodium carbonate and run for 30 minutes. Finally wash off and dry.

The title compounds fix to the cotton via covalent bonds and hence provide a permanent increase in the SPF of the treated cotton fabric.

Example 8

A suitable pad-batch method is as follows:

Apply a solution containing 2% owf absorber compound, 5% owf sodium carbonate and 0.1% owf wetting agent (e.g. a nonylphenyl polyethoxylate) by padding to achieve a pick-up of 100%. The padded fabric is then batched (cold) overnight in a sealed plastic wrap. Finally wash off and dry.

The title compounds fix to the cotton via covalent bonds and hence provide a permanent increase in the SPF of the treated cotton fabric.

Example 9

A suitable alternative pad-batch method is as follows:

Apply a solution containing 2% owf absorber compound, 5% owf sodium carbonate and 0.1% owf wetting agent (e.g. a nonylphenyl polyethoxylate) by padding to achieve a pick-up of 100%. The padded fabric is then steamed for 30 minutes at 100°–105° C. to achieve fixation. Finally wash off and dry.

The title compounds fix to the cotton via covalent bonds and hence provide a permanent increase in the SPF of the treated cotton fabric.

2. Di-fluoro-mono-chloro-pyrimidine UV absorber derivatives on wool

Example 10

These compounds may be applied to wool by either exhaustion or pad methods.

A suitable exhaustion method is as follows:

Apply 2% owf absorber compound, 10% owf sodium sulphate, 1.0% owf acetic acid and 0.1% owf wetting agent (e.g. a nonylphenyl polyethoxylate); LR 30:1. Start at 40° C., raise to 70° C. over 20 minutes, hold at 70° C. for 30 minutes; then raise the temperature to the boil and boil for 15 minutes. Finally wash off and dry.

The title compounds fix to the wool via covalent bonds and hence provide a permanent increase in the SPF of the treated wool fabric.

Example 11

A suitable alternative pad-batch method is as follows:

Apply a solution containing 2% owf absorber compound, 5% owf urea and 0.1% owf wetting agent (e.g. a nonylphenyl polyethoxylate) by padding to achieve a pick-up of 100%. The padded fabric is then steamed for 30 minutes at 100°–105° C. to achieve fixation. Finally wash off and dry.

The title compounds fix to the wool via covalent bonds and hence provide a permanent increase in the SPF of the treated wool fabric.

In each of the following examples, a substance was applied to a fabric of less than 200 g/m$^2$ and the resultant combination was tested to obtain measurements on the change in SPF, whether the combination exhibited colourfastness to washing and whether the combination exhibited colourfastness to light.

UVR and SPF Measurement Methods

The ultra-violet transmission (direct and diffuse) of the sample was measured over the UVR spectral range of 290 to 380 nm using a Cary 3 UV-visible spectrophotometer fitted with an integrating sphere attachment. A Schott UG#11 filter was used to eliminate the effects of fluorescence from the fluorescent whitening agents (FWA) (if any) in the sample.

The SPF's (sun protection factors) were estimated for 2 mm "off skin" by a method developed in a research project initiated by the Lidcombe Hospital Dermatology Center. The method is fully described in the publication entitled: "A Comparative Study of Fabric Protection against Ultraviolet-Induced Erythema Determined by Spectrophotometric and Human Skin Measurements", by S. W. Menzies, P. B. Lukins, G. E. Greenoak, P. J. Walker, M. T. Pailthorpe, J. M. Martin, S. K. David and K. E. Georgouras, Journal of Photodermatology, Photoimmunology and Photomedicine, 1992: 8(4), 157–163.

The ultra-violet transmission data, and the calculated SPF's, were measured on the fabric in a dry relaxed state (i.e. not stretched).

The predicted SPF's are indicative of the SPF's to be found on human skin.

Colourfastness to washing

The colourfastness to washing of the untreated fabrics and UVR absorber treated fabrics was determined by the methods described in AS 2001.4.15 "Determination of Colourfastness to Washing: Test A: Colourfastness to Simulated Hand Laundering in the Presence of Soap".

Colourfastness to Light

The colourfastness to light of the untreated and UVR absorber treated fabrics was determined by the methods described in AS 2001.4.21 "Determination of Colourfastness to Light using an Artificial Light Source (Mercury Vapour, Tungsten Filament, Internally Phosphor-Coated Lamp)". Exposures were conducted for a total of 858 hours (circa 35 days) for which the ISO Blue Standard Rating was 7.

Details of all the chemicals mentioned in the specification are available from the indicated proprietor.

And extensive search of the literature and enquires made of textile chemical suppliers in Australia showed that there a very few water-soluble (or water-dispersable) UV absorbers commercially available.

There are no UV absorbers commercially available for cotton.

Ciba-Geigy market two UV absorbers:

CIBAFAST N, which is described as "an agent to protect polyamide fibres against detrimental effects of light and heat and to improve the light fastness of dyeings of these fibres.

CIBAFAST W, which is described as "an agent to protect wool against detrimental effects of light and heat".

Sandoz market one UV absorber for polyester:

FADEX F LIQUID, which is used to improve the light fastness of dyeings of polyester, particularly those used in automobile upholstery.

Neither manufacturer makes any claim in their technical literature regarding the use of these products to increase the SPF of fibre or fabric.

Example 12

Cibafast W (CFW) on wool.

Cibafast W is applied according to the exhaustion method. Firstly, it is dissolved in a bath and the product (fabric/fibre) has a wetting agent applied to it before it is inserted into the bath. The bath is boiled for approximately 1 hour to enable the Cibafast W to enter the fabric/fibre.

Utilising the above method, it is noted that Cibafast W is not glued to the fabric but instead enters the fibres of fabric and in effect is bonded to the fibres due to the affinity between Cibafast W and the wool fibres.

In all the following examples, the "blank dyed" samples referred to are samples that have been put through the identical application process used for the relevant UVR absorber, but without the active agent (UVR absorber). The "blank dyed" sample often exhibits an improved SPF due primarily to shrinkage effects incurred in the process.

Using the application method described above, the following results were obtained.

The stated "Suggested SPF" is the mean SPF less the 95% confidence limit rounded down to the nearest multiple of five. Thus the suggested SPF is conservative.

TABLE 1

| FABRIC DETAILS | SPF RESULTS (8 Samples) | SUGGESTED SPF |
|---|---|---|
| Control Wool | 42 ± 12 | 25+ |
| Repeat | 34 ± 9 | 25+ |
| Blank Dyed | 64 ± 9 | 55+ |
| Repeat | 84 ± 30 | 50+ |
| 1% CFW | 108 ± 19 | 85+ |
| 2% CFW | 108 ± 20 | 85+ |
| 5% CFW | 127 ± 26 | 100+ |
| 10% CFW | 102 ± 18 | 80+ |

From Table 1 it is apparent that Cibafast W has caused a significant improvement in the SPF ratings for this wool fabric. An application of 1% CFW is sufficient to double the blank dyed SPF value.

The fastness of Cibafast W on wool to washing and light is given in the following Table 2.

TABLE 2

| FABRIC DETAILS | INITIAL SPF | SPF AFTER WASHING | SPF AFTER 858 HOURS EXPOSURE |
|---|---|---|---|
| Control Wool | 36 ± 3 (30+) | 42 ± 18 (20+) | 59 ± 20 (35+) |
| Blank Dyed | 84 ± 30 (50+) | 99 ± 29 (70+) | 135 ± 40 (95+) |
| 1% CFW | 130 ± 50 (80+) | 125 ± 34 (90+) | 198 ± 112 (85+) |
| 2% CFW | 174 ± 76 (95+) | 180 ± 85 (90+) | 147 ± 26 (100+) |

From Table 2 it is apparent that the improved SPF ratings obtained by using Cibafast W are "fast" to both washing and to light.

Example 13

Fadex F on Polyester

Method of Application

Fadex F was first applied to polyester at 100° C. in a Goodbrand-Jeffries Dyemaster machine (S/N 13011) Laboratory Dyeing Machine. However, it was noted that polyester required an increased temperature in order to effectively be impregnated with Fadex F. Accordingly, Fadex F was applied at 130° C. in the Labortex "Rapid" Dyeing Machine Model #8. A person skilled in the art would be familiar with such a method.

The results of impregnating polyester with Fadex F are provided in Table 3.

TABLE 3

| FABRIC DETAILS | SPF RESULTS (4 Samples) | SUGGESTED SPF |
| --- | --- | --- |
| Control PES | 15 ± 1 | 10+ |
| Repeat | 15 ± 2 | 10+ |
| Blank Dyed | 18 ± 2 | 15+ |
| 1% Fadex | 39 ± 4 | 35+ |
| 2% Fadex F | 48 ± 7 | 40+ |
| 5% Fadex F | 47 ± 8 | 35+ |

From Table 3 it is apparent that Fadex F causes a significant improvement in the SPF ratings of polyester fabric.

Fadex F was then tested for fastness to washing and light.

TABLE 4

| FABRIC DETAILS | INITIAL SPF | SPF AFTER WASHING | SPF AFTER 858 HOURS EXPOSURE |
| --- | --- | --- | --- |
| Control PES | 15 ± 1 (10+) | 15 ± 2 (10+) | 18 ± 4 (10+) |
| Blank Dyed | 18 ± 2 (15+) | 19 ± 5 (10+) | not tested |
| 1% Fadex F | 39 ± 4 (35+) | 37 ± 3 (30+) | 38 ± 3 (30+) |
| 2% Fadex F | 48 ± 7 (40+) | 45 ± 4 (40+) | 49 ± 6 (40+) |
| 5% Fadex F | 47 ± 8 (35+) | 52 ± 7 (40+) | 44 ± 8 (35+) |

From the data given in Table 4, it is apparent that the improved SPF ratings endowed by Fadex F on polyester are fast to both washing and exposure to light.

Example 14

Fadex F on Nylon

Because a temperature of 130° C. was required for the application of Fadex F to polyester, Fadex F was applied to nylon at 130° C. centigrade in the Labortex "Rapid" Dyeing Machine.

The results of the application of Fadex F to nylon at 130° C. centigrade indicated that the colour of the nylon was effected and accordingly, a temperature of 100° C. was then adopted.

The Fadex F was thus applied to nylon at 100° C. centigrade in the Dyemaster Dyeing Machine and was applied at 1% and 2% treatment levels. The treated nylon samples were only slightly yellowish in hue after the treatment. The results of the treatment of nylon with Fadex F are given in Table 5.

TABLE 5

| FABRIC DETAILS | INITIAL SPF | SPF AFTER WASHING | SPF AFTER 858 HOURS EXPOSURE |
| --- | --- | --- | --- |
| Control Nylon | 10 ± 3 (5+) | 15 ± 1 (10+) | 10 ± 2 (5+) |
| Repeat | 9 ± 1 (5+) | | |
| Blank Dyed | 16 ± 2 (10+) | 14 ± 1 (10+) | 14 ± 3 (10+) |
| 1% Fadex F | 29 ± 8 (20+) | 28 ± 2 (25+) | 21 ± 5 (15+) |
| 2% Fadex F | 29 ± 6 (20+) | 31 ± 10 (20+) | 28 ± 6 (20+) |

From Table 5 it can be seen that Fadex F significantly improves the SPF ratings of the nylon fabric employed. In addition, the results indicate that the improvement in SPF ratings caused by the addition of Fadex F is fast to both washing and exposure to light.

Example 15

Fadex F on 65/35

Fadex F was applied to 65/35 polyester/cotton fabric at 130° C. in the Labortex "Rapid" dyeing machine. The results are given in Table 6.

TABLE 6

| FABRIC DETAILS | SPF RESULTS (4 Samples) | SUGGESTED SPF |
| --- | --- | --- |
| Control PES/CO | 15 ± 2 | 10+ |
| Blank Dyed | 15 ± 5 | 10+ |
| 1% Fadex | 28 ± 6 | 20+ |
| 2% Fadex F | 25 ± 5 | 20+ |
| 3% Fadex F | 24 ± 4 | 20+ |

From Table 6 it is apparent that Fadex F causes a significant improvement in the SPF ratings of this polyester/cotton fabric. The Fadex F treated fabric, were then assessed for fastness to washing and to light. The results are given in Table 7.

TABLE 7

| FABRIC DETAILS | INITIAL SPF | SPF AFTER WASHING |
| --- | --- | --- |
| Control PES | 15 ± 2 (10+) | NOT TESTED |
| Blank dyed | 15 ± 5 (10+) | 15 ± 1 (10+) |
| 1% FADEX F | 68 ± 6 (20+) | 27 ± 5 (20+) |
| 2% FADEX F | 25 ± 5 (20+) | 26 ± 4 (20+) |
| 3% FADEX F | 24 ± 4 (20+) | 24 ± 4 (20+) |

From Table 7 it is apparent that Fadex F when applied to 65/35 polyester/cotton improves the SPF ratings and the SPF ratings are fast to washing. Additional experimentation also indicates that the SPF ratings are fast to exposure to light with the SPF after 858 hours exposure being maintained at 20+.

Example 16

Fadex F was also applied to secondary cellulose acetate and triacetate and as with nylon provided increases in SPF ratings similar to those provided for nylon. The Dyemaster Dyeing Machine method of application was also found to be suitable.

From the above experiments it is apparent that light weight materials of less than 200 grams per square meter, such as nylon, wool and polyester can be provided with significantly increased values of SPF protection by the addition of either Cibafast W or Fadex F as previously outlined. The resultant and combination of fibre material and UVR absorber is both fast to washing and to exposure to light.

Both Cibafast W and Fadex F are UVR absorbers and have previously been used to protect particular fibres against detrimental effects of light and heat. From a vast number of different chemical substances it has been found that Cibafast W and Fadex F increased the SPF rating of the previously mentioned fibres to which they were applied, and at the same time avoided deleterious effects to the fibres. Other chemical substances used, for example, Cibafast N (a registered trade name of CIBA-GEIGY) not only failed to increase the SPF rating of the treated fabric but in many cases adversely affected the colour of the fabric so that it would be unsuitable for use commercially.

TABLE 8

| SAMPLE | SPF RESULTS (8 Samples) | SUGGESTED SPF |
|---|---|---|
| Untreated Fabric | 9 ± 1 | 5+ |
| Blank Dyed | 14 ± 2 | 10+ |
| 1% Cibafast N | 17 ± 1 | 15+ |
| 2% Cibafast N | 16 ± 2 | 10+ |

Table 8 provides the results of applying Cibafast N to nylon using the Dyemaster Laboratory Dyeing machine. From Table 8 it is apparent that Cibafast N did not significantly increase the SPF rating of the treated fabric and experiments also revealed that the Cibafast N induced a "greenish" colour into the white nylon fabric.

Example 17

Application of Compound 1 on cotton
(Compound 1 is 2,4-difluoro-5-chloro-6-phenylamino pyrimidine)

Compound 1 was prepared by the condensation of aniline (Fluka) and 2,4,6-trifluoro-5-chloropyrimidine (Sandoz) by the method of Example 2.

17(a) Compound 1 was applied to 3 g samples of a woven plain weave cotton fabric (145 g/m² : Charles Parsons, Sydney) by exhaustion from ethanol. The formulation was as follows:

| 1% | o.w.f. Compound 1 |
|---|---|
| LR: | 30:1 |
| Temp: | 20° C. |
| Time: | 10 minutes |
| Cure: | Fan forced over; 90° C.; 15 minutes. |
| Wash: | Thorough cold rinse; then hot rinse (60° C.) |
| Dry: | Fan forced oven; 60° C.; 30 minutes. |

The results are summarized in the Table 9.

TABLE 9

| SPF RESULTS FOR WOVEN FABRIC | | |
|---|---|---|
| SAMPLE DETAILS | SPF RESULTS | SUGGESTED SPF |
| 100% cotton control (4) | 28.0 ± 3.2 | 20+ |
| 1% Compound 1 (8) | 51.3 ± 7.7 | 40+ |

These preliminary small scale experiments show that Compound 1 has the capability of significantly increasing the SPF of this 100% cotton woven fabric.

17(b) Compound 1 was applied to 3 g samples of a woven plain weave cotton fabric (145 g/m² : Charles Parsons, Sydney) by exhaustion from aqueous emulsion. The formulation was as follows:

| 1% | o.w.f. Compound 1 (emulsion) |
|---|---|
| LR | 40:1 |
| Temp: | Start at 40° C., Raise to 65° C. over 30 minutes; hold 30 minutes; raise to 98° C., hold 30 minutes. |
| Wash: | Thorough cold rinse; then hot rinse (60° C.) |
| Dry: | Fan forced oven; 60° C.; 30 minutes. |

The results are summarized in the Table 10.

TABLE 10

| SPF RESULTS FOR WOVEN FABRIC | | |
|---|---|---|
| SAMPLE DETAILS | SPF RESULTS | SUGGESTED SPF |
| 100% cotton control (4) | 28.0 ± 3.2 | 20+ |
| Blank Treated (4) | 26.6 ± 2.7 | 20+ |
| 1% Compound 1 (8) | 42.6 ± 8.5 | 35+ |
| 2% Compound 1 (4) | 44.4 ± 4.9 | 35+ |

These small scale experiments show that Compound 1 has the capability of significantly increase the SPF of this 100% cotton woven fabric.

UV-Transmission

The UV-transmission of a 5 g/l ethanolic solution of Compound 1 was measured in a 5 mm quartz cell using a Cary 3 UV-Visible spectrophotometer.

Figure 1:
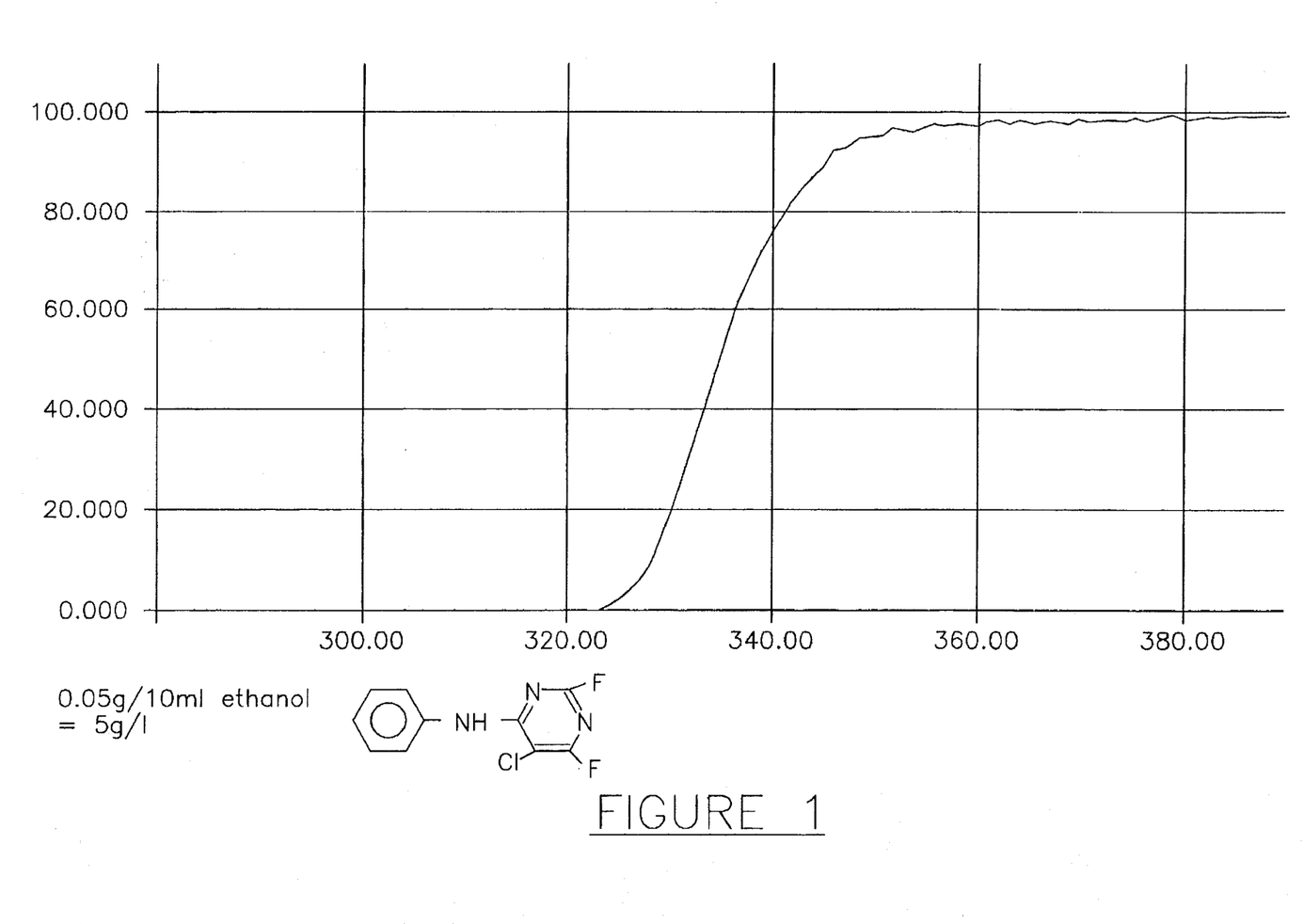
FIG. 1 is a graph of the UV-transmission of a 5 g/L ethanol solution of the compound of Example 1 as measured in a 5 mm quartz cell in a Cary 3 UV-visible spectrophotometer.

The results are given in FIG. 1.

It can be readily seen that Compound 1 begins to absorb strongly below 340 nm; ie in the UVB region. Thus this type of compound absorbs the very harmful UVB rays YET will not significantly interfere with the function of fluorescent whitening agents (FWA). Thus the treated cotton remains a full white.

On the basis of these results it can be seen that 1% o.w.f. Compound 1 gives a very significant increase in the SPF of this 100% cotton fabric.

Example 18

Application of Compound 2 on Cotton
(Compound 2 is p-(2,4-dichloro-s-triazine-6-ylamino)-o-methyl-phenyl sulphonic acid sodium salt)

In the following application recipe it has been assumed that Compound 2 has been formulated as 100% reactive compound.

In the determination of wash-fastness of the treated fabric, soap was replace by 1 g/l of OMO (OMO is a trade mark of Unilever plc).

18(a) Compound 2 was applied to 5 g samples of woven plain weave 100% cotton fabric (145 g/m² : Charles Parsons, Sydney) by exhaustion in a Goodbrand-Jeffries Laboratory Dyeing Machine. The formulation was as follows:

| 50 g/l Sodium chloride (NaCl) | |
|---|---|
| x % | o.w.f. Compound 2 |
| LR | 40:1 |
| Temp: | 50° C. |
| Time: | 30 minutes |
| Then: | Add 5 g/l Sodium carbonate |
| Run: | 30 minutes of 50° C. |
| Wash: | Thorough cold rinse; then hot rinse (60° C.) |
| Dry: | Fan forced over; 60° C.; 60 minutes. |

The results are summarized in the Table 11.

TABLE 11

SPF RESULTS FOR WOVEN FABRIC

| SAMPLE DETAILS | SPF RESULT | SUGGESTED SPF |
|---|---|---|
| 100% cotton control (4) | 29.5 ± 2.6 | 25+ |
| Blank treated sample (4) | 26.4 ± 7.3 | 15+ |
| 1% Compound 2 (8) | 41.1 ± 5.6 | 35+ |
| 2% Compound 2 (8) | 47.7 ± 11.8 | 35+ |

These preliminary small scale experiments show that Compound 2 has the capability of significantly increasing the SPF of this 100% cotton woven fabric.

18(b) Winch Application

3% Compound 2 was applied to 600 g of a woven plain weave 100% cotton fabric (Charles Parsons, Sydney) by exhaustion in a laboratory scale winch dyeing machine. The formulation was as follows:

| | 50 g/l Sodium chloride (NaCl) |
|---|---|
| 3% | o.w.f. Compound 2 |
| LR | 30:1 |
| Temp: | 50° C. |
| Time: | 30 minutes |
| Then: | Add 5 g/l Sodium carbonate |
| Run: | 30 minutes of 50° C. |
| Wash: | Thorough cold rinse; then hot rinse (60° C.) |
| Dry: | Tumble dry: 60° C.; 60 minutes. |

The results are summarized in the Table 12.

TABLE 12

SPF RESULTS FOR WOVEN FABRIC

| SAMPLE DETAILS | SPF RESULT | SUGGESTED SPF |
|---|---|---|
| 100% cotton control (8) | 24.5 ± 3.6 | 20+ |
| 3% Compound 2 (8) | 41.0 ± 4.4 | 35+ |

These which dyeing experiments show that Compound 2 has significantly increased the SPF of this 100% cotton woven fabric.

The fastness to washing and to light of the Compound 2 (winch) treated 100% cotton was then evaluated and the results are given in Table 13.

TABLE 13

FASTNESS RESULTS

| SAMPLE DETAILS | SPF RESULT | SUGGESTED SPF |
|---|---|---|
| 100% cotton control (8) | 24.5 ± 3.6 | 20+ |
| 3% Compound 2 (8) | 41.0 ± 4.4 | 35+ |
| After 1 wash/drying cycle (8) | 39.9 ± 4.5 | 35+ |
| After 5 wash/drying cycle (8) | 41.8 ± 3.6 | 35+ |
| After 70 hours light exposure | | |
| Blank (Untreated) (8) | 32.1 ± 5.3 | 25+ |
| Treated (8) | 50.1 ± 12.2 | 35+ |
| After 162 hours light exposure (8) | 43.0 ± 5.8 | 35+ |

18(c) Pad-Batch Application to knitted fabric

3% Compound 2 was applied to circa 35 g of a knitted 100% cotton fabric (Avon 100% cotton; Size XXL; Sunsafe 30+ : This fabric would have a weight of 180–190 g/cm$^2$) by padding using a laboratory scale padding machine. The formulation was as follows:

| 3% | w/w Comuound 2 |
|---|---|
| | 5 g/l sodium carbonate |
| Add-on: | 90% |
| Temp: | Room temperature |
| Batch: | 6 hours (cold) in sealed plastic bags |
| Wash: | Thorough cold rinse; then hot rinse (60° C.) |
| Dry: | Tumble dry: 60° C.; 60 minutes. |

The results are summarized in the Table 14.

TABLE 14

PAD - BATCH RESULTS ON KNITTED FABRIC

| SAMPLE DETAILS | SPF RESULT | SUGGESTED SPF |
|---|---|---|
| 100% cotton control (8) | 33.7 ± 5.7 | 25+ |
| Blank padded sample (8) | 51.5 ± 4.5 | 45+ |
| 2.7% Compound 2 (8) | 103.1 ± 17.0 | 85+ |

The "blank" padded sample has shrunk, giving rise to the higher SPF of this specimen. The Compound 2 treated sample has a greatly improved SPF over both the control and blank samples.

These pad-batch dyeing experiments show that Compound 2 has significantly increased the SPF of the 100% cotton knitted fabric.

18(d) Pad-Batch Application to woven fabric

3% Compound 2 was applied to circa 25 g of a woven 100% cotton fabric (Charles Parsons) by padding using a laboratory scale padding machine. the formulation was as follows:

| 3% | w/w Comuound 2 |
|---|---|
| | 5 g/l sodium carbonate |
| Add-on: | 90% (Hence 2.7% applied) |
| Temp: | Room temperature |
| Batch: | 6 hours (cold) in sealed plastic bags |
| Wash: | Thorough cold rinse; then hot rinse (60° C.) |
| Dry: | Tumble dry: 60° C.; 60 minutes. |

The results are summarized in the Table 15.

TABLE 15

SPF RESULTS FOR PADDED WOVEN FABRIC

| SAMPLE DETAILS | SPF RESULT | SUGGESTED SPF |
|---|---|---|
| 100% cotton control (8) | 24.5 ± 3.6 | 20+ |
| Blank padded woven (8) | 30.9 ± 4.5 | 25+ |
| 2.7% Compound 2 (8) | 59.5 ± 6.9 | 50+ |

These pad-batch dyeing experiments show that Compound 2 has significantly increased to SPF of this 100% cotton woven fabric.

On the basis of these results it can be seen that Compound 2 can be conveniently applied to cotton fabrics (either knitted or woven) by both "exhaustion" and "pad-batch" methods.

The treated fabrics are fast to both washing and to light.

The treated fabrics have significantly higher SPFs than the control fabrics (and blank treated fabrics).

Compound 2 beings to absorb strongly below 359 nm, ie in the UVB region. UVB is most damaging to the skin and the principal cause of skin cancer.

By not absorbing significantly above 350 nm, Compound 2 does not inhibit the function of fluorescent whitening agents (FWA) and hence the fabric remains a bright white yet has a high SPF.

We claim:

1. A method of increasing the SPF rating of cellulosic or protein fiber or fabric, comprising applying, by exhaustion or pad-methods, to said cellulosic or protein fiber or fabric one or more UVR absorber compounds of formulae (III) or (IV):

wherein A is —NH— or —SO$_2$— and when A is —NH—, B is selected from a compound of formulae (i)–(vii) as follows:

and when A is —SO$_2$—, B is selected from a compound of formulae (viii)–(x) as follows:

(viii) —CH=CH—OSO$_3$H (ix) —CH$_2$—CH$_2$—OSO$_3$H (x) —NH—CH$_2$—CH$_2$—OSO$_3$H;

R is independently selected from —OH, —NH$_2$, —SO$_3$M$^+$, —SO$_3$H, alkyl, alkoxy, alkanoyl, alkylcarboxylate, —S-alkyl, —CF$_3$, and —N-di-alkyl;

n=0, 1, 2, 3, or 4;

M$^+$=cation;

X=is independently selected from H, Cl, F, or Br; and

Y=X or R.

2. A method of claim 1 wherein said cellulosic or protein fiber or fabric has a density of less than 200 g/m$^2$ whereby an application of less than 3% (based on weight of fiber or fabric) of a compound of formulae (III) or (IV) produces an SPF rating of greater than 20.

3. A method of claim 2 wherein an application of less than 2% of a compound of formula (III) or (IV) produces an SPF rating of greater than 20.

4. A method of claim 1 wherein said cellulosic or protein fiber is cotton and wherein said method comprises applying a compound of formula (IV) where A is —NH—, B is a compound of formula (ii), X is Cl, n is 2 and one R is in the 3-position of the phenyl ring and is —CH$_3$ and the other R is in the 4-position and is —SO$_3$—Na$^+$.

5. An article of clothing comprising a plurality of fibers and one or more UVR absorber compounds, wherein the plurality of fibers have a density of less than 200 grams per square meter and the SPF rating of the article has been increased to at least 20 by the addition of less than 3% (based on weight of fiber) of one or more UVR absorber compounds of formulae (III) or (IV):

wherein A is —NH— or —SO$_2$— and when A is —NH—, B is selected from a compound of formulae (i)–(vii) as follows:

(i)

(ii)

(iii)

(iv)

(v)

—CO—C=CH₂ (vi)
     |
     Br

—CO—CH=CH₂; (vii)

and when A is —SO₂—, B is selected from a compound of formulae (viii)–(x) as follows:

(viii) —CH=CH—OSO₃H
(ix) —CH₂—CH₂—OSO₃H
(x) —NH—CH₂—CH₂—OSO₃H;

R is independently selected from —OH, —NH₂, —SO₃M⁺, —SO₃H, alkyl, alkoxy, alkanoyl, alkylcarboxylate, —S-alkyl, —CF₃, and —N-di-alkyl;

n=0, 1, 2, 3, or 4;

M⁺=cation;

X=is independently selected from H, Cl, F, or Br; and

Y=X or R.

6. An article of clothing of claim 5, wherein the SPF rating of the article has been increased to at least 20 by the addition of less than 2% UVR absorber.

7. An article of clothing comprising a plurality of fibers and one or more UVR absorber compounds of formulae (III) or (IV):

(III)

(IV)

wherein A is —NH— or —SO₂— and when A is —NH—, B is selected from a compound of formulae (i)–(vii) as follows:

(i)

(ii)

(iii)

(iv)

(v)

—CO—C=CH₂ (vi)
     |
     Br

—CO—CH=CH₂; (vii)

and when A is —SO₂—, B is selected from a compound of formulae (viii)–(x) as follows:

(viii) —CH=CH—OSO₃H
(ix) —CH₂—CH₂—OSO₃H
(x) —NH—CH₂—CH₂—OSO₃H;

R is independently selected from —OH, —NH₂, —SO₃M⁺, —SO₃H, alkyl, alkoxy, alkanoyl, alkylcarboxylate, —S-alkyl, —CF₃, and —N-di-alkyl;

n=0, 1, 2, 3, or 4;

M⁺=cation;

X=is independently selected from H, Cl, F, or Br; and

Y=X or R.

8. Clothing or fabric in which the SPF rating has been increased to 20 or more prepared by a method which comprises applying, by exhaustion or pad-methods, to clothing or fabric one or more UVR absorber compounds of formulae (III) or (IV):

(III)

(IV)

wherein A is —NH— or —SO₂— and when A is —NH—, B is selected from a compound of formulae (i)–(vii) as follows:

(i)

(ii)

$$CH_2-CH-CH_2 \text{ (epoxide)}$$ (iii)

(iv)

(v)

$$-CO-\underset{Br}{C}=CH_2$$ (vi)

$$-CO-CH=CH_2;$$ (vii)

and when A is —SO₂—, B is selected from a compound of formulae (viii)–(x) as follows:

(viii) —CH=CH—OSO₂H
(ix) —CH₂—CH₂—OSO₃H
(x) —NH—CH₂—CH₂—OSO₃H;

R is independently selected from —OH, —NH₂, —SO₃M⁺, —SO₃H, alkyl, alkoxy, alkanoyl, alkylcarboxylate, —S-alkyl, —CF₃, and —N-di-alkyl;

n=0, 1, 2, 3, or 4;

M⁺=cation;

X=is independently selected from H, Cl, F, or Br; and

Y=X or R.

* * * * *